(12) United States Patent  
Clarke et al.

(10) Patent No.: US 9,125,595 B2
(45) Date of Patent: Sep. 8, 2015

(54) SYSTEM AND INSOLE FOR MEASURING INFORMATION FROM THE FOOT OF A USER AND RELATED METHOD OF PROVIDING SAME

(71) Applicant: SmartMove, Inc., Fort Collins, CO (US)

(72) Inventors: Eric Clarke, Fort Collins, CO (US); Douglas E. Bartlett, Fort Collins, CO (US); Harold L. Baeverstad, Jr., Fort Collins, CO (US)

(73) Assignee: SmartMove, Inc., Fort Collins, CO (US)

( * ) Notice: Subject to any disclaimer, the term of this patent is extended or adjusted under 35 U.S.C. 154(b) by 77 days.

(21) Appl. No.: 14/137,485

(22) Filed: Dec. 20, 2013

(65) Prior Publication Data

US 2014/0174205 A1    Jun. 26, 2014

Related U.S. Application Data

(60) Provisional application No. 61/797,953, filed on Dec. 20, 2012.

(51) Int. Cl.

| | |
|---|---|
| *G01L 1/12* | (2006.01) |
| *A61B 5/103* | (2006.01) |
| *A61B 5/00* | (2006.01) |

(52) U.S. Cl.
CPC ............. *A61B 5/1036* (2013.01); *A61B 5/1038* (2013.01); *A61B 5/6807* (2013.01); *A61B 2562/0252* (2013.01)

(58) Field of Classification Search
CPC ..................... A61B 2562/0247; A61B 5/1036; A61B 5/6807; A61B 2562/164; A61B 2562/182
USPC ............... 73/780, 862.041–862.046, 862.626
See application file for complete search history.

(56) References Cited

U.S. PATENT DOCUMENTS

| 4,862,743 | A | * | 9/1989 | Seitz ............................... 73/172 |
|---|---|---|---|---|
| 6,033,370 | A | * | 3/2000 | Reinbold et al. .............. 600/595 |
| 7,191,644 | B2 | * | 3/2007 | Haselhurst et al. ............. 73/172 |
| 8,569,935 | B1 | * | 10/2013 | Kosierkiewicz .............. 310/363 |
| 2009/0297756 | A1 | * | 12/2009 | Dehn .............................. 428/68 |
| 2010/0004566 | A1 | * | 1/2010 | Son et al. ....................... 600/592 |
| 2010/0271051 | A1 | * | 10/2010 | Sankai et al. ................. 324/679 |
| 2011/0098605 | A1 | * | 4/2011 | deGreef et al. ............... 600/592 |
| 2013/0213145 | A1 | * | 8/2013 | Owings et al. ........... 73/862.046 |

* cited by examiner

*Primary Examiner* — Max Noori
(74) *Attorney, Agent, or Firm* — Bryan Cave LLP

(57) ABSTRACT

An insole can include: an upper conductive ground plane layer; an upper compressible insulating layer physically coupled to the upper conductive ground plane layer; a conductive sensor layer physically coupled to the upper compressible insulating layer, the conductive sensor layer comprising one or more sensors are configured to a force applied to the insole by the foot; a lower compressible insulating layer physically coupled to conductive sensor layer; a lower conductive ground plane layer physically coupled to the lower compressible insulating layer and electrically coupled to the upper conductive ground plane layer; and at least one computational unit communicatively coupled to the one or more sensors. The upper conductive ground plane layer and the lower conductive ground plane layer are configured to substantially electrically shield the upper compressible insulating layer, the conductive sensor layer, and the lower compressible insulating layer from the shoe and the foot. Other embodiments are disclosed.

20 Claims, 7 Drawing Sheets

SYSTEM AND INSOLE FOR MEASURING INFORMATION FROM THE FOOT OF A USER AND RELATED METHOD OF PROVIDING SAME

CROSS-REFERENCE TO RELATED APPLICATIONS

This application claims the benefit of U.S. Provisional Application No. 61/797,953, filed Dec. 20, 2012. U.S. Provisional Application No. 61/797,953 is incorporated herein by reference.

STATEMENT REGARDING FEDERALLY SPONSORED RESEARCH OR DEVELOPMENT

The U.S. Government has a paid-up license in this invention and the right in limited circumstances to require the patent owner to license other on reasonable terms as provided by the terms of 5R44DK083229-04 awarded by National Institutes of Health.

FIELD OF THE INVENTION

This invention relates generally to systems for determining information regarding a foot and activity of a user, and relates more particularly to insoles and systems for determining forces and other information related to the user and methods of providing the same.

DESCRIPTION OF THE BACKGROUND

In many sports and other activities, people find it useful to measure and analyze physical conditions caused by a foot in order to improve physical performance. In addition, people with medical conditions may want to monitor various parameters related to walking and other movements of their feet.

A number of electrical devices are known for measuring a force caused by a foot. However, these devices have various drawbacks. Some devices require custom-built footwear to be constructed in order to measure forces caused by the foot, and cannot readily be used with an athlete's existing footwear. Many devices require an inconvenient and unsightly wire connection to a measurement apparatus, which is either obtrusively worn on the body or which must be carried along to a new location every time the athlete moves. In addition, various wireless measurement devices exist but these devices can be expensive and/or can lack reliable and accurate measurements.

Accordingly, a need or potential for benefit exists for an unobtrusive device capable of sensing a physical condition caused by a foot and communicating information regarding the foot to the user.

BRIEF DESCRIPTION OF THE DRAWINGS

To facilitate further description of the embodiments, the following drawings are provided in which.

For simplicity and clarity of illustration, the drawing figures illustrate the general manner of construction, and descriptions and details of well-known features and techniques may be omitted to avoid unnecessarily obscuring the invention. Additionally, elements in the drawing figures are not necessarily drawn to scale. For example, the dimensions of some of the elements in the figures may be exaggerated relative to other elements to help improve understanding of embodiments of the present invention. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the invention described herein are, for example, capable of operation in other orientations than those illustrated or otherwise described herein.

The terms "couple," "coupled," "couples," "coupling," and the like should be broadly understood and refer to connecting two or more elements or signals, electrically, mechanically and/or otherwise. Two or more electrical elements may be electrically coupled but not be mechanically or otherwise coupled; two or more mechanical elements may be mechanically coupled, but not be electrically or otherwise coupled; two or more electrical elements may be mechanically coupled, but not be electrically or otherwise coupled. Coupling may be for any length of time, e.g., permanent or semi-permanent or only for an instant.

"Electrical coupling" and the like should be broadly understood and include coupling involving any electrical signal, whether a power signal, a data signal, and/or other types or combinations of electrical signals. "Mechanical coupling," "physically coupled," and the like should be broadly understood and include mechanical coupling of all types.

The absence of the word "removably," "removable," and the like near the word "coupled," and the like does not mean that the coupling, etc. in question is or is not removable.

DETAILED DESCRIPTION OF EXAMPLES OF EMBODIMENTS

Some embodiments can concern an insole for a shoe to be worn on a foot of a user. The insole can include: an upper conductive ground plane layer; an upper compressible insulating layer physically coupled to the upper conductive ground plane layer; a conductive sensor layer physically coupled to the upper compressible insulating layer, the conductive sensor layer comprising one or more sensors that are configured to measure a force applied to the insole by the foot of the user; a lower compressible insulating layer physically coupled to conductive sensor layer; a lower conductive ground plane layer physically coupled to the lower compressible insulating layer and electrically coupled to the upper conductive ground plane layer; and at least one computational unit communicatively coupled to the one or more sensors. The upper conductive ground plane layer and the lower conductive ground plane layer are configured to substantially electrically shield the upper compressible insulating layer, the conductive sensor layer, and the lower compressible insulating layer from the shoe and the foot of the user. The one or more sensors are configured to measure at least one of a first change in a first distance between the upper conductive ground plane layer and the one or more sensors and a second change in a second distance between the lower conductive ground plane layer and the one or more sensors. The at least one computational unit is configured to determine a force applied to the insole using the at least one of the first change in the first distance or the second change in the second distance.

The same or different embodiments can concern a system for measuring information regarding the foot of a user. The system can include: an insole having: a first protective cover configured to be a first outer layer of the insole; a first grounding layer, a top surface of the first grounding layer is physically coupled to a bottom surface of the first protective cover; a first compressible insulating layer, a top surface of the first compressible insulating layer is physically coupled to a bottom surface of the first grounding layer; a sensor layer comprising a heel sensor and a ball sensor, a top surface of the sensor layer is physically coupled to a bottom surface of the first compressible insulating layer; a second compressible insulating layer, a top surface of the second compressible insulating layer is physically coupled to a bottom surface of the sensor layer; a second grounding layer, a top surface of the second grounding layer is physically coupled to a bottom surface of second compressible insulating layer, the second grounding layer is also electrically coupled to the first grounding layer such that the first grounding layer and the second grounding layer substantially electrically isolate the insole from the shoe and the foot of the user; and a second protective cover, a top surface of the second protective cover is physically coupled a bottom surface of the second grounding layer and configured to be a second outer layer of the insole; and at least one computational unit communicatively coupled to the heel sensor and the ball sensor. The first grounding layer, the second grounding layer and the sensor layer are electrically coupled to form a three-layer capacitor and the ball sensor and the heel sensor are configured to measure changes in capacitance between at least two of the first grounding layer, the second grounding layer and the sensor layer when a force is applied to the insole. The at least one computational unit is configured to determine a magnitude of the force applied to the insole using at least the changes in the capacitance between the at least two of the first grounding layer, the second grounding layer and the sensor layer.

Various embodiments concern a method of providing an insole for a shoe. The insole can be configured to be placed in the shoe and the shoe is configured to be placed on a foot of a user. The method can include: providing an upper conductive ground plane layer; providing an upper compressible insulating layer; physically coupling the upper compressible insulating layer to the upper conductive ground plane layer; providing a conductive sensor layer, the conductive sensor layer comprising one or more sensors that are configured to measure a force applied to the insole; physically coupling the upper compressible insulating layer to conductive sensor layer; providing a lower compressible insulating layer; physically coupling the lower compressible insulating layer to conductive sensor layer; providing a lower conductive ground plane layer; physically coupling the lower conductive ground plane layer to the upper conductive ground plane layer; electrically coupling the lower conductive ground plane layer to the upper conductive ground plane layer such that the upper conductive ground plane layer and the lower conductive ground plane layer are configured to substantially electrically shield the upper compressible insulating layer, the conductive sensor layer, and the lower compressible insulating layer from the shoe and the foot of the user; and providing at least one computational unit. The one or more sensors can be configured to measure at least one of a first change in a first distance between the upper conductive ground plane layer and the one or more sensors or a second change in a second distance between the lower conductive ground plane layer and the one or more sensors. The at least one computational unit is configured to determine a force applied to the insole using at least one of the first change in the first distance and the second change in the second distance.

Figure 1:
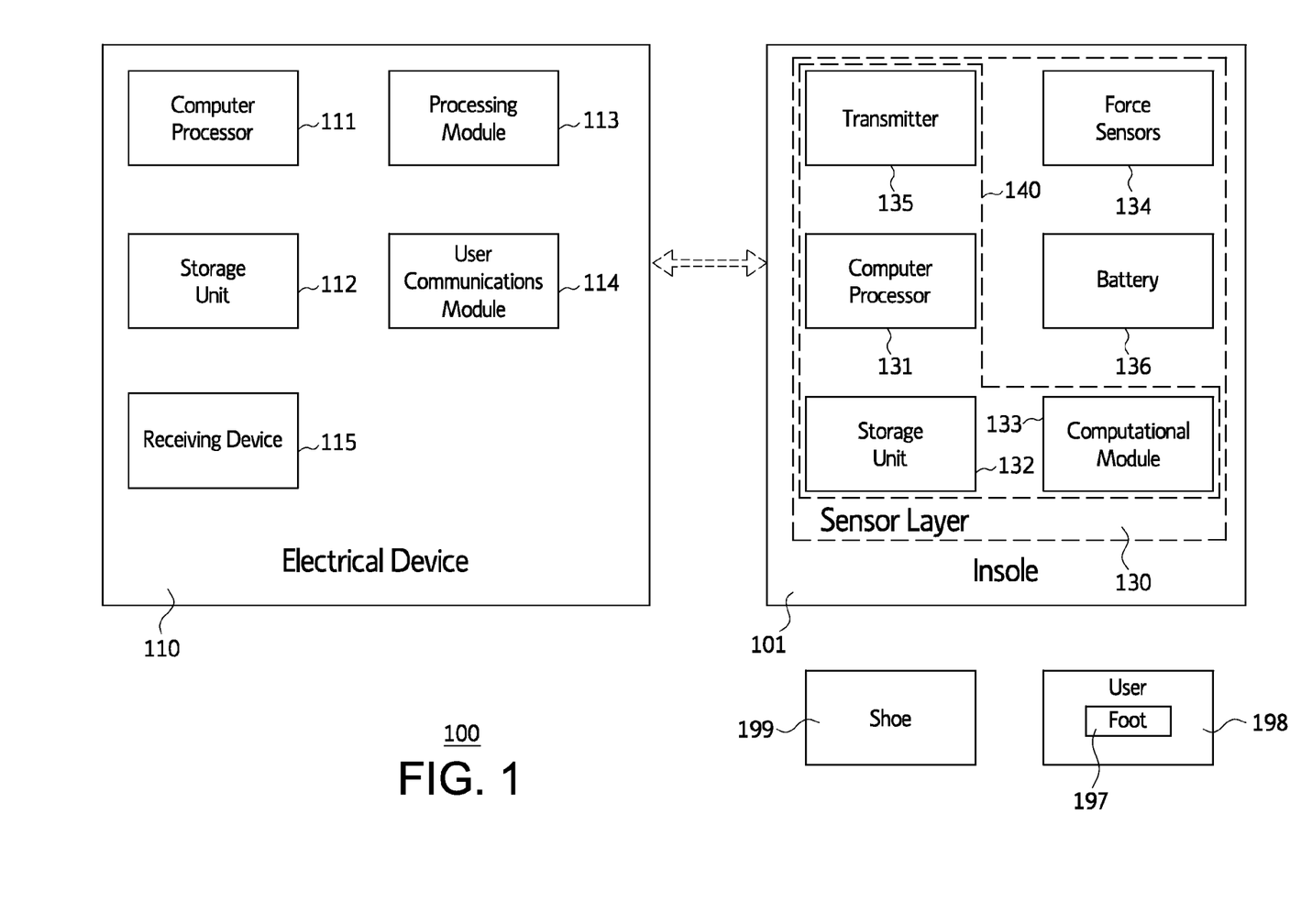
FIG. 1 illustrates an exemplary block diagram of a system for determining information from a foot of a user, according to a first embodiment.
Figure 2:
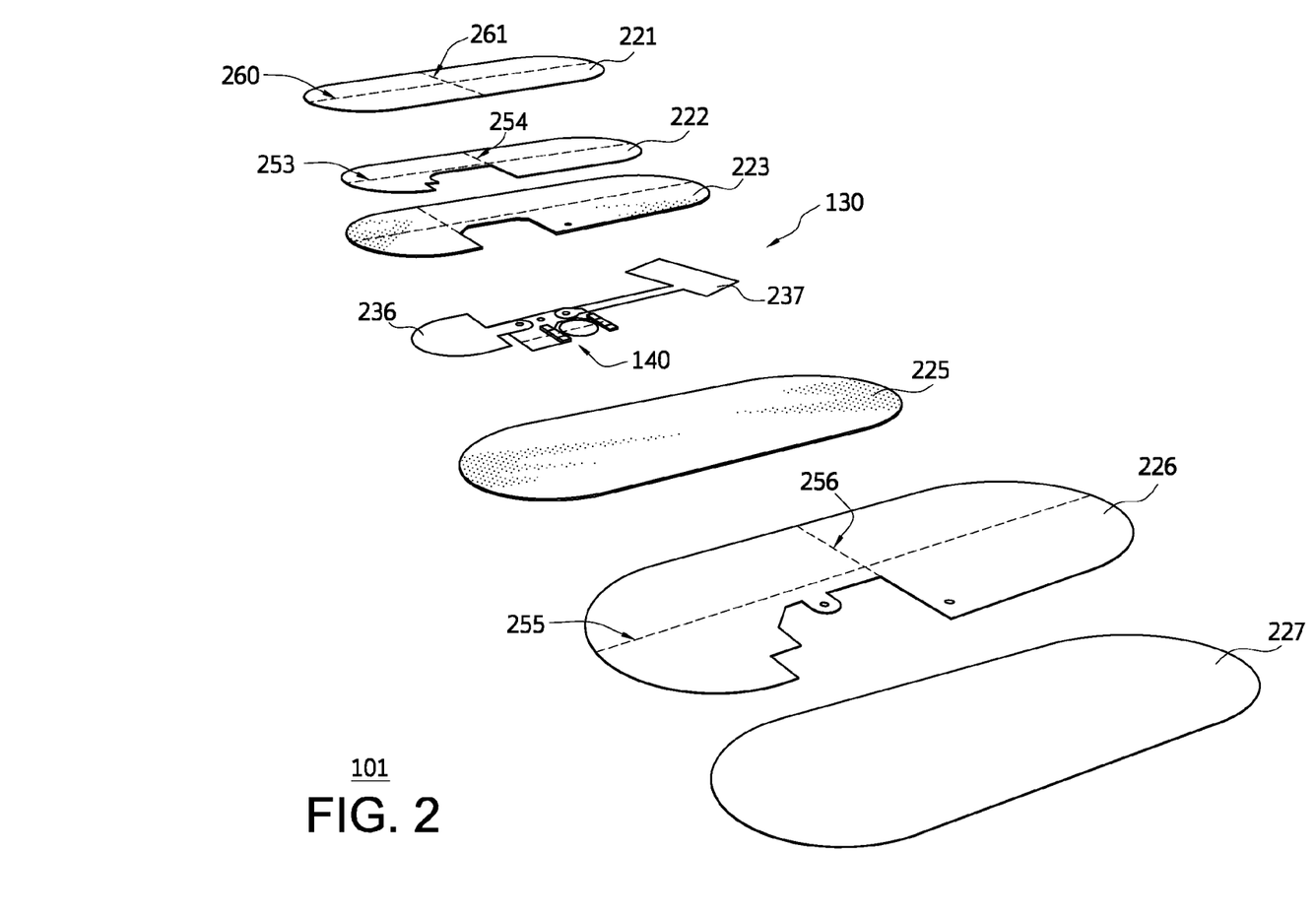
FIG. 2 illustrates a top perspective blown-up view of an exemplary insole of the system of FIG. 1, according to the first embodiment.
Figure 3:
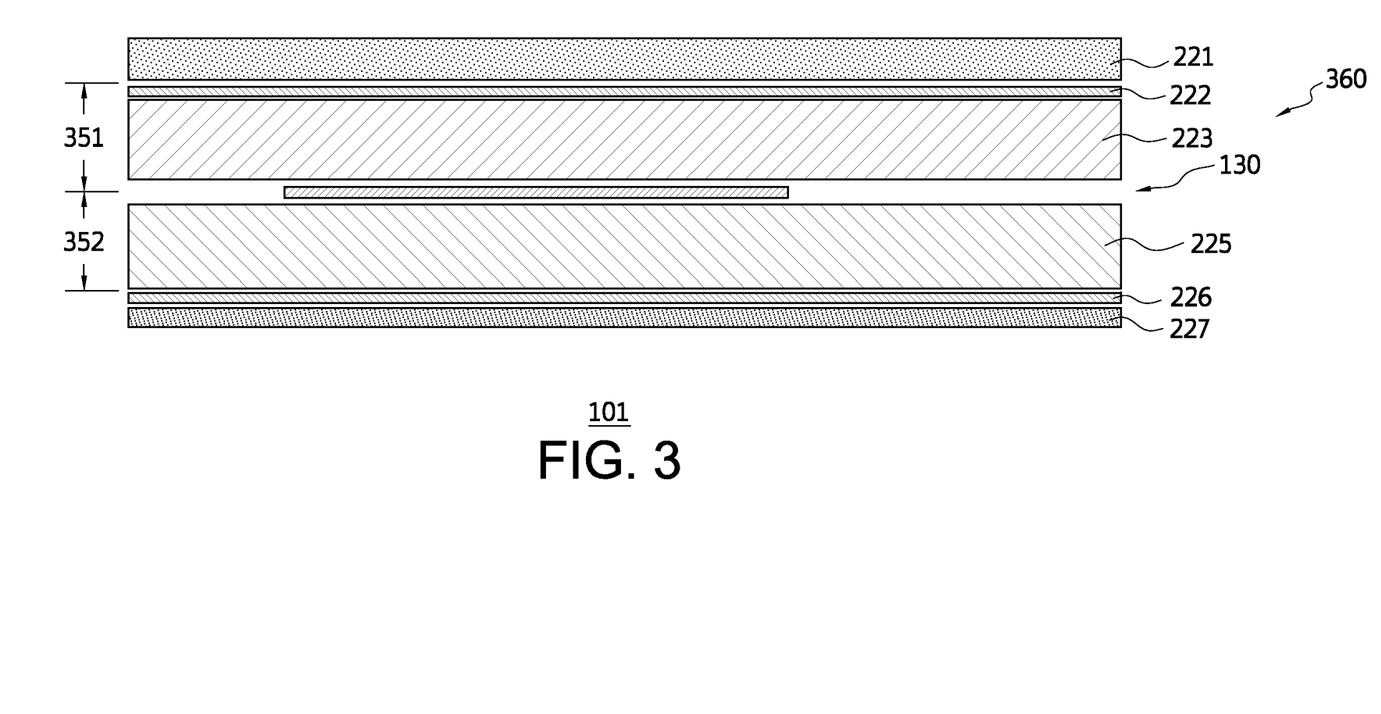
FIG. 3 illustrates a side cut-away view of the insole of FIG. 2, according to the first embodiment.
Figure 4:
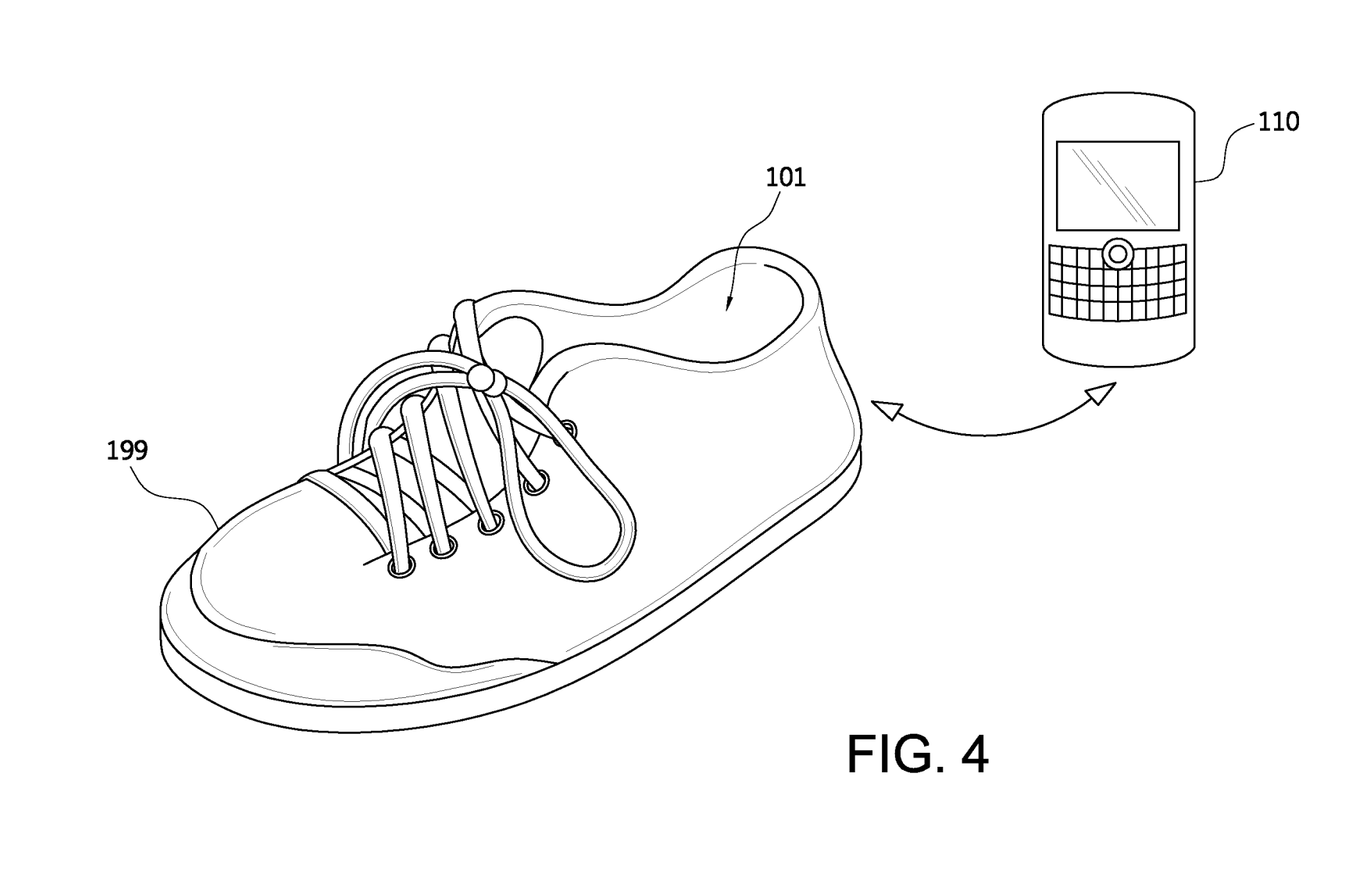
FIG. 4 illustrates an exemplary diagram of the electrical device of FIG. 1 and the insole of FIGS. 1 and 2 in a shoe, according to the first embodiment.

Turning to the drawings, FIG. 1 illustrates an exemplary block diagram of a system 100 for determining information from the foot 197 of a user 198, according to a first embodiment. FIG. 2 illustrates a top perspective blown-up view of an exemplary insole 101 for a shoe 199 to be worn on foot 197 of user 198, according to the first embodiment. FIG. 3 illustrates a side cut-away view of insole 101, according to the first embodiment. FIG. 4 illustrates an exemplary diagram of electrical device 110 and insole 101 in shoe 199, according to the first embodiment. System 100 and insole 101 are merely exemplary and are not limited to the embodiments presented herein. System 100 and insole 101 can be employed in many different embodiments or examples not specifically depicted or described herein.

Referring to FIGS. 1-4, in some embodiments, a system 100 for determining information regarding foot 197 (or feet) of user 198 can include: (a) at least one insole 101 configured to be placed in shoe 199; and (b) one or more electrical device 110.

In some examples, electrical device 110 can include: (a) a computer processor (e.g., a computational unit) 111; (b) a storage unit 112; (c) a processing module 113 configured to be stored in storage unit 112 and executed using computer processor 111; (d) a user communications module 114; and (e) a receiving device 115 (i.e., a remote communication device).

In the same or different examples, insole 101 can include: (a) a protective cover 221 (i.e., a comfort layer) configured to be an outer layer of insole 101; (b) a grounding layer 222 (e.g., a conductive ground plane layer) physically coupled to protective cover 221; (c) a compressible insulating layer 223 (e.g., a compressible dielectric layer) physically coupled to grounding layer 222; (d) a sensor layer (e.g., a conductive sensor layer) 130 physically coupled to compressible insulating layer 223; (e) a compressible insulating layer 225 physically coupled to sensor layer 130; (f) a grounding layer 226 physically coupled to compressible insulating layer 225; (g) a protective cover 227 configured to be an outer layer of insole 101 and physically coupled to grounding layer 226. In some examples, grounding layer 222 can be similar or identical to grounding layer 226; compressible insulating layer 223 can be similar or identical to compressible insulating layer 225; and/or protective cover 221 can be similar or identical to protective cover 227.

In many examples, protective layer 221 can be configured to physically touch foot 197. As used herein, protective layer 221 physically touching the foot of the user or similar terms refers to either directly touching the foot of the user or physically touching the foot through one or more intermediate layers (e.g., socks, nylons, bandages, Band-Aids, and/or braces).

In many examples, as illustrated in FIG. 3, a top surface of grounding layer 222 can be physically coupled to a bottom surface of protective cover 221. A top surface of compressible insulating layer 223 can be physically coupled to a bottom surface of grounding layer 222. A top surface of sensor layer 130 can be physically coupled to a bottom surface of compressible insulating layer 223. A top surface of compressible insulating layer 225 can be physically coupled to a bottom surface of sensor layer 130. A top surface of grounding layer 226 can be physically coupled to a bottom surface of compressible insulating layer 225. A top surface of protective cover 227 can be physically coupled to a bottom surface of grounding layer 226. In some examples, the various layers can be physically coupled together with glue, another adhesive, thermally bonded or laminated together.

In numerous embodiments, a length 253 of grounding layer 222 is substantially equal to a length 260 of insole 101 and a width 254 of grounding layer 222 is substantially equal to a width 261 of insole 101. In some examples, a surface area of grounding layer 222 is substantially equal to a surface area of insole 101.

In the same of different example, a length 255 of grounding layer 226 is substantially equal to length 260 of insole 101 and a width 256 of grounding layer 226 is substantially equal to width 261 of insole 101. In some examples, a surface area of grounding layer 226 is substantially equal to the surface area of insole 101.

In other examples, grounding layers 222 and 226 can only partially cover the surface area of insole 101. The purpose of the open area of grounding layers 222 and 226 can be to avoid shielding an antenna of transmitter 135 (FIG. 1). In various embodiments, compressible insulating layer 223 and 225 can only extend beyond the edges of ball sensor 236 and heel sensor 237 by an adequate distance to contain the electrical fields (e.g., four times a thickness of compressible insulating layer 223 and 225). These openings can to support the transmitter 135 and can have nothing to do with the force sensor itself. The shape of grounding layers 222 and 226 can be typically be the same. This configuration allows a single die to cut both grounding layers 222 and 226. However, this is configuration is not necessary as long as the shielding requirements are met.

In various embodiments, protective cover 221 can include a compressible foam and other materials to increase the comfort of insole 101 for user 198 when user 198 is wearing shoe 199 with insole 101 in shoe 199. Protective cover 227 can include an abrasion resistant coat.

In some examples, grounding layers 222 and 226 can include cloth (nylon, rayon, polyester, etc.) with interwoven conductive fibers (e.g., silver, or copper threads), conductive rubber materials, sheets of metalized Mylar® material, or a conductive ink flex layer. In the same or different examples, grounding layers 222 and 226 can comprise conductive fabrics.

Compressible insulating layers 223 and 225 can include sheet rubber compounds, compressible plastic materials or alternative open or closed cell foams (e.g., Poron material). In the same or different examples, compressible insulating layers 223 and 225 can comprise compressible insulating materials.

Parts of sensor layer 130 and/or sensors 134 can include a cloth (nylon, rayon, polyester, etc.) with interwoven conductive fibers (e.g., silver, or copper threads), conductive ink flex circuit, low cost off the shelf sensors, metalized Mylar® material, a hybrid assembly using several of these options or conductive rubber.

Sensor layer 130 can include: (a) a computer processor 131; (b) storage unit 132; (c) computational module configured to be stored in storage unit 132 and executing using computer processor 131; (d) one or more force sensors 134; (e) transmitter 135; and (f) battery 136 configured to provide electrical power to computer processor 131, storage unit 132, force sensors 134, and transmitter 135. In the example shown in FIGS. 1-4, computer processor 131, storage unit 132, force sensors 134, computational module 133, and transmitter 135 are part of sensor layer 130. In other embodiments, at least one of computer processor 131, storage unit 132, force sensors 134, computational module 133, and transmitter 135 can be located in other layers of insole 101 or be located in shoe 199.

The sensor layer 130 includes ball sensor 236 and heel sensor 237 which are electrically coupled to an electronics module 140. Electronics module 140 can include the transmitter 135, processor 131, and storage unit (132 and computational module 133. Electronics module 140 can be configured measures the capacitance between each of ball sensor 236 and heel sensor 237.

In some examples, transmitter 135 (i.e., a communication device) can be a wireless transmitter (or transceiver), and receiving device 115 can be a wireless receiver (or transceiver). In some examples, electrical signals can be transmitted using WI-FI (wireless fidelity), the IEEE (Institute of Electrical and Electronics Engineers) 802.11 wireless protocol or the Bluetooth 4.1 (with Bluetooth low energy) wireless protocol. In further examples, these signals can be transmitted via a Zigbee (802.15.4), Z-Wave, or a proprietary wireless standard. In other examples, transmitter 135 can transmit electrical signals using a cellular connection.

In various embodiments, force sensors 134 can be configured to determine change(s) in a first distance 351 between grounding layer 222 and sensor layer 130 and change(s) in a second distance 352 between grounding layer 226 and sensor layer 130. In some examples, force sensors 134 can determine the first change in the first distance and the second change in the second distance. Computational module 133 can be configured to determine a force applied to insole 101 by foot 197 (and/or the ground) using at least the change(s) in first distance 351 and/or change(s) in second distance 352.

In some examples, force sensors 134 can include: (a) ball sensor 236; and (b) heel sensor 237. In other examples, force sensors 134 can include one sensor or three or more force sensors.

In some embodiments, ball sensor 236 can be located in a region of sensor layer 130 under where a ball of foot 197 is located when the user 198 is wearing shoe 199 with insole 101. Heel sensor 237 is located in a region of sensor layer 130 under where a heel of foot 197 is located when user 198 is wearing shoe 199 with insole 101. In some examples, ball sensor 236 can determine the change(s) in the first distance 351 and/or second distance 352 at the region around or at the ball of foot 197 and heel sensor 237 can determine the change (s) in the first distance 351 and/or second distance 352 at the region around or at the heel of foot 197. Computational module 133 can be configured to determine the force applied to insole 101 by foot 197 (and/or the ground) using any number of these four measurements.

Figure 5:
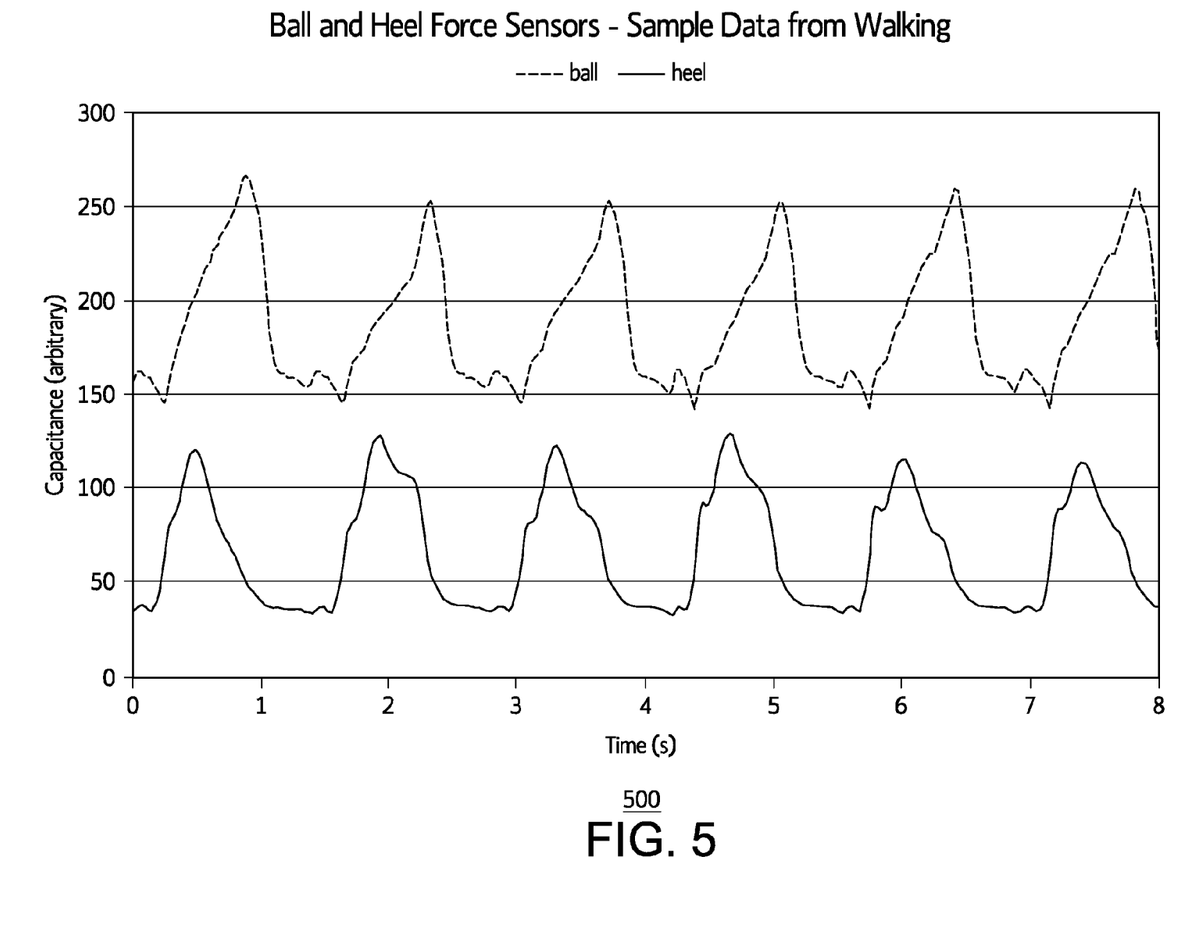
FIG. 5 illustrates an exemplary graph of the change in capacitance when a user is walking using the system of FIG. 1.

Grounding layer 222, grounding layer 226 and sensor layer 130 can be configured to form a three-layer capacitor 360. In many embodiments, force sensors 134 can measure the change in capacitance between sensor layer 130 and grounding layer 222 and/or 226 caused by the compression of insole 101 by foot 197 and/or the ground. For example, when user 198 takes a step on the ground, at least parts of insole 101 will be compressed by the force applied by foot 197. The portion of insole 101 around the heel of foot 197 can be compressed at the same or a different time than the portion of the insole around the ball of foot 197. This compression causes distance 351 and 352 to be decreased and the capacitance between sensor layer 130 and grounding layer 222 and/or 226 to change. FIG. 5 illustrates an exemplary graph 500 of the change in capacitance for ball sensor 236 and heel sensor 237 when user 198 is walking. As illustrated in FIG. 5, the capacitance at ball sensor 236 and then heel sensor 237 increases and decreases at a regular intervals as user 198 raises and lowers foot 197 when walking at a constant velocity. In these examples, capacitance is inversely proportional to the distance between the capacitor plates. Capacitance is proportional to the area of the force sensors 134.

Referring back to FIGS. 1-4, grounding layer 222, and grounding layer 226 are configured to substantially electrically shield compressible insulating layer 223, a sensor layer 130, and compressible insulating layer 225 from any electrical charges or electrical currents from shoe 199, foot 197, user 198, the ground, and the environment in general around insole 101. In many examples, grounding layer 222 is electrically coupled to grounding layer 226 such that grounding layers 222 and 226 substantially electrically isolate force sensors 134 from any electrical charge on the shoe 199, foot 197, user 198, the ground, and the environment in general around insole 101. For example, grounding layers 222 and 226 can be configured to substantially electrically block the upper compressible insulating compressible insulating layer 223, a sensor layer 130, and a compressible insulating layer 225 from any parasitic capacitance from foot 197.

Grounding layers 222 and 226 can be electrically coupled by folding a single layer of fabric to form the two layers, by wrapping a conductive material (same as these layers or different) around the side of insole 101, by stapling through the layers with a conductive staple, or by separately connecting these two layers to the same electrical node of electronics module 140.

Using grounding layers 222 and 226 to electrically shield compressible insulating layer 223, sensor layer 130, and compressible insulating layer 225 provides many benefits over traditional force sensors. The human body is not electrically grounded (even though many traditional force sensor assume it is) and the body can acquire a charge (e.g., from sliding on a plastic chair). In existing force sensors, these electrical charges can be transferred to the insole and interfere with electrical circuitry and devices in the insole.

Figure 6:
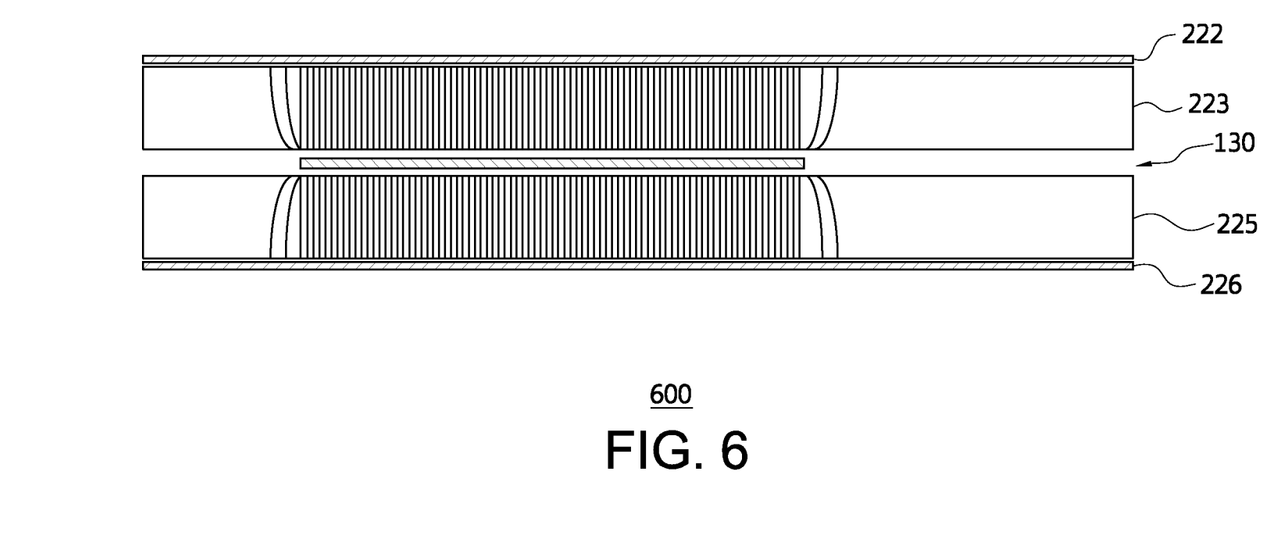
FIG. 6 illustrates an exemplary diagram of the electrical field lines created by the insole of FIGS. 1 and 2.

FIG. 6 illustrates an exemplary diagram 600 of the electrical field lines created by insole 101. As shown in FIG. 6, the electrical field lines created by insole 101 are contained inside of grounding layers 222 and 227 and substantially no electrical field lines external to grounding layers 222 and 227 are penetrating grounding layers 222 and v and no electrical field line from insole are seeping outside grounding layers 222 and 227. Accordingly, grounding layers 222 and 227 are shielding insole 101 from external electrical charges and fields.

Usually, external electrical charge or fields can make reading from traditional force sensors unreliable and inaccurate. Some traditional force sensors use wires coupled to expensive and bulky equipment to acquire accurate force measurement but these traditional force sensors are limited in the their range of uses because of their cost, size, and limited mobility. The use of grounding layers 222 and 226 in system 100 for electrical isolation can eliminate the problems caused by static charge or other voltages or currents on the foot of the user and other charges, voltages, and current on the shoe, the ground, or the user. Thus, system 100 can provide more accurate and reliable force measurement compared to existing force sensors while using less expensive parts.

The electronics module 140 located at sensor layer 130 (e.g., transmitter 135, computer processor 131, storage unit 132) can be provided through a flex circuit assembly, electronics/sensor hybrid assembly and or a highly integrated set of electronics. Conventional printed circuit board electronics using surface mount (SMT) or through hole components or a multi-chip module can also be used.

Furthermore, additional functionality could be added to insole 101 through changes in sensor geometries, sensor placement, additional sensors and/or how the electronics couple and/or communicates with force sensors 134.

In some examples, computational module 133 can be configured to determine a magnitude of the force applied to insole 101 based upon the measurements by force sensors 134. For example, computational module 133 can be configured to determine a magnitude of the force applied to insole 101 using at least the changes in capacitance of the capacitor formed by insole 101.

In the same or different examples, computational module 133 can also calculate the activity of the user (running, walking, sitting, etc.), the posture of user 198, and/or the energy expended by the user. Computational module 133 can communicated all or part of this information (or the raw data or semi-processed raw data) to transmitter 135, which transmits (e.g., wirelessly) the information to receiving device 115 of electrical device 110.

Receiving device 115 can communicate the information to processing module 113. Processing module 113 can perform additional processing to information from computational module 133. For example, if the information received from the raw data (or a sample of the raw data), processing module 113 can calculate the applied force, the activity of the user, the posture of the user, and/or the energy expended by the user.

Processing module 113 can communicate information related to the force applied and other information to insole 101 to user communication module 114. User communication module 114 can communicate the information to user 198 (e.g., display information on a screen of electrical device 110).

The terms "electrical device" should be broadly understood and include electrical devices of all types and designs (e.g., MP3 players, telephones, and audio-visual media players). There are many portable electrical devices available, including those manufactured by Sony Corp., Philips Corp., Audiovox Corp., Microsoft Corp., Nokia Corp., Research-in- Motion, Inc. (e.g., the Blackberry® device), Samsung Group (e.g., Galaxy® device), Amazon.com, Inc. (e.g., Kindle® device), and Apple Computer, Inc. (e.g., iPod® MP3 player, iPhone™ device and iPad™ device). In other examples, the term "electrical device" can refer to a single computer (e.g., a laptop or desktop), single server, or a cluster or collection of servers.

As used herein, "computer processor" means any type of computational circuit, such as but not limited to a microprocessor, a microcontroller, a controller, a complex instruction set computing (CISC) microprocessor, a reduced instruction set computing (RISC) microprocessor, a very long instruction word (VLIW) microprocessor, a graphics processor, a digital signal processor, or any other type of processor or processing circuit capable of performing the desired functions.

In some examples, storage units 112 and 132 can include any type of computer memory (e.g., read only memory (ROM) and/or random access memory (RAM)). When computer processor 131 in insole 101 is active, program instructions stored on stored in storage unit 132 are executed by computer processor 131. A portion of the program instructions, in storage unit 132, can be suitable for carrying out computational module 133 of FIG. 1 and method 700 of FIG. 7.

Figure 7:
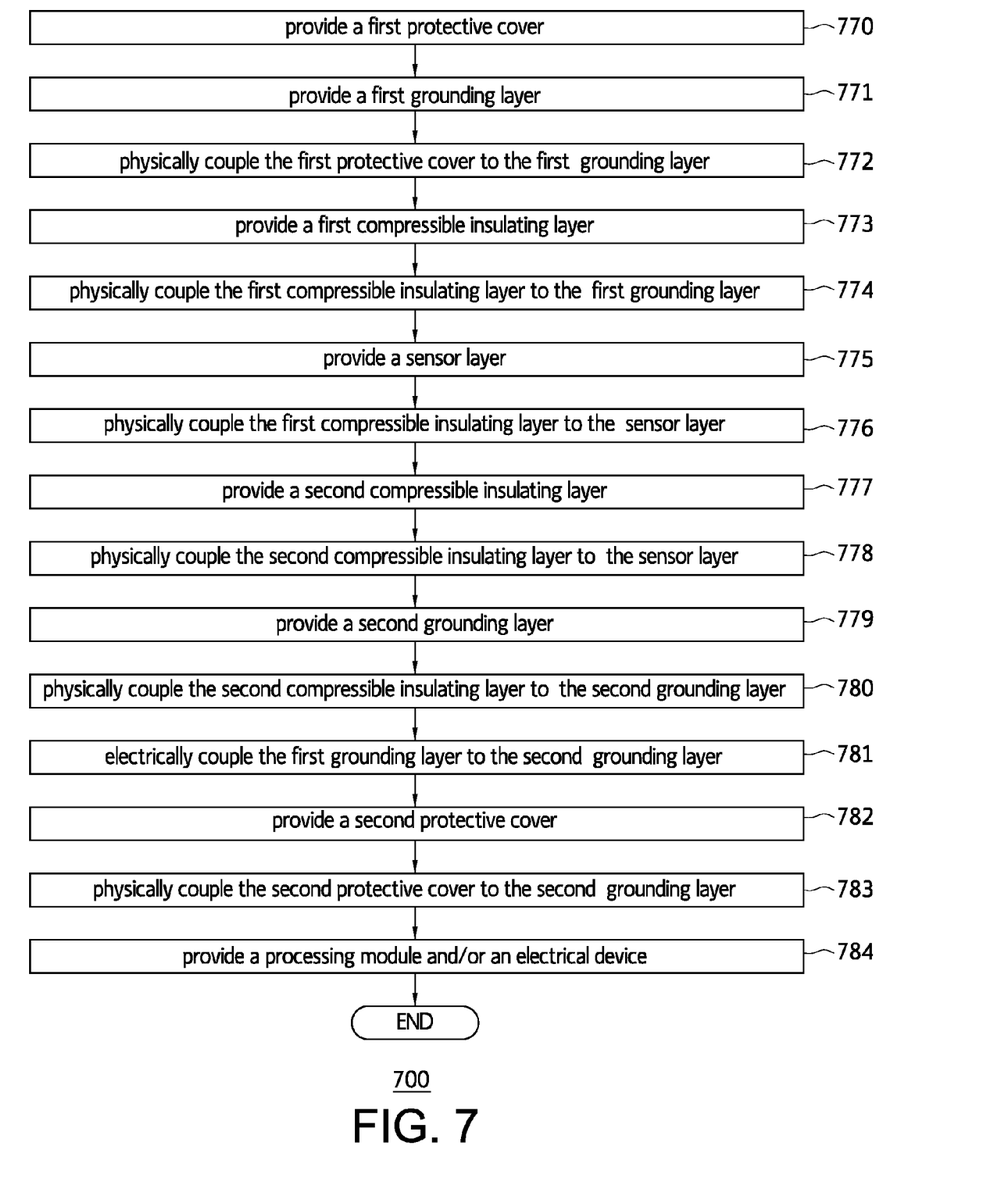
FIG. 7 illustrates a flow chart for an embodiment of a method of providing a system for measuring a force and other information related to a foot of a user.

FIG. 7 illustrates a flow chart for an embodiment of a method 700 of providing a system for measuring force(s) applied and other information related to a foot of a user. Method 700 can also concern a method of providing an insole for a shoe. Method 700 is merely exemplary and is not limited to the embodiments presented herein. Method 700 can be employed in many different embodiments or examples not specifically depicted or described herein. In some embodiments, the activities, the procedures, and/or the processes of method 700 can be performed in the order presented. In other embodiments, the activities, the procedures, and/or the processes of method 700 can be performed in any other suitable order. In still other embodiments, one or more of the activities, the procedures, and/or the processes in method 700 can be combined or skipped.

Referring to FIG. 7, method 700 includes an activity 770 of providing a first protective cover. As an example, the first protective cover can be similar or identical to protective cover 221 of FIG. 2.

Method 700 in FIG. 7 continues with an activity 771 of providing a first grounding layer. As an example, the first grounding layer can be similar or identical to grounding layer 222 of FIG. 2.

Subsequently, method 700 of FIG. 7 includes an activity 772 of physically coupling the first protective cover to the first grounding layer. As an example, the physically coupling of the first protective cover to the first grounding layer can be similar or identical to the physically coupling of protective cover 221 to grounding layer 222, as illustrated in FIG. 3. In many examples, a top surface of the first grounding layer can be coupled to a bottom surface of the first protective cover. In various embodiments, the first protective cover and the first grounding layer can be glued, laminated, or thermally bonded together.

Next, method 700 of FIG. 7 includes an activity 773 of providing a first compressible insulating layer. As an example, the first compressible insulating layer can be similar or identical to compressible insulating layer 223 of FIG. 2.

Method 700 in FIG. 7 continues with an activity 774 of physically coupling the first compressible insulating layer to the first grounding layer. As an example, the physically coupling of the first compressible insulating layer to the first grounding layer can be similar or identical to the physically coupling of protective compressible insulating layer 223 to grounding layer 222, as illustrated in FIG. 3. In many examples, a top surface of the first compressible insulating layer can be coupled to a bottom surface of the first grounding layer. In various embodiments, the first compressible insulating layer and the first grounding layer can be glued, laminated, or thermally bonded together.

Subsequently, method 700 of FIG. 7 includes an activity 775 of providing a sensor layer. As an example, the sensor layer can be similar or identical to sensor layer 130 of FIGS. 1 and 2. In some examples, providing the sensor layer can include providing a computer processor, a storage unit, a computational module, one or more force sensors, a transmitter, and/or a battery. In many examples, the force sensors and the other elements of the sensor layer can be similar or identical to force sensors 134 and the other elements of sensor layer 130 of FIGS. 1 and 2.

Next, method 700 of FIG. 7 includes an activity 776 of physically coupling the first compressible insulating layer to the sensor layer. As an example, the physically coupling of the first compressible insulating layer to the sensor layer can be similar or identical to the physically coupling of sensor layer 130 to compressible insulating layer 223, as illustrated in FIG. 3. In many examples, a top surface of the sensor layer can be coupled to a bottom surface of the first compressible insulating layer. In various embodiments, the first compressible insulating layer and the sensor layer can be glued, laminated, or thermally bonded together.

Method 700 in FIG. 7 continues with an activity 777 of providing a second compressible insulating layer. As an example, the second compressible insulating layer can be similar or identical to compressible insulating layer 225 of FIG. 2.

Subsequently, method 700 of FIG. 7 includes an activity 778 of physically coupling the second compressible insulating layer to sensor layer. As an example, the physically coupling of the second compressible insulating layer to sensor layer can be similar or identical to the physically coupling of sensor layer 130 to compressible insulating layer 225, as illustrated in FIG. 3. In many examples, a bottom surface of the sensor layer can be coupled to a top surface of the second compressible insulating layer. In various embodiments, the second compressible insulating layer and sensor layer can be glued, laminated, or thermally bonded together.

Next, method 700 of FIG. 7 includes an activity 779 of providing a second grounding layer. As an example, the second grounding layer can be similar or identical to grounding layer 226 of FIG. 2.

Method 700 in FIG. 7 continues with an activity 780 of physically coupling the second compressible insulating layer to the second grounding layer. As an example, the physically coupling of the second compressible insulating layer to the second grounding layer can be similar or identical to the physically coupling of protective compressible insulating layer 225 to grounding layer 226, as illustrated in FIG. 3. In many examples, a bottom surface of the second compressible insulating layer can be coupled to a top surface of the second grounding layer. In various embodiments, the second compressible insulating layer and the second grounding layer can be glued, laminated, or thermally bonded together.

Subsequently, method 700 of FIG. 7 includes an activity 781 of electrically coupling the first grounding layer to the second grounding layer. In some examples, the first grounding layer and the second grounding layer can be electrically coupled similar or identical to the electrical coupling of grounding layer 222 and grounding layer 226. In various examples, the first grounding layer and the second grounding layer can be electrically coupled to substantially electrically shield the first compressible insulating layer, the sensor layer, and the second compressible insulating layer from any electrical charges or electrical currents from shoe and foot of the user, the ground, and the environment around the insole.

Next, method 700 of FIG. 7 includes an activity 782 of providing a second protective cover. As an example, the second protective cover can be similar or identical to protective cover 227 of FIG. 2.

Method 700 in FIG. 7 continues with an activity 783 of physically coupling the second protective cover to the second grounding layer. As an example, the physically coupling of the second protective cover to the second grounding layer can be similar or identical to the physically coupling of protective cover 227 to grounding layer 226, as illustrated in FIG. 3. In many examples, a bottom surface of the second grounding layer can be coupled to a top surface of the second protective cover. In various embodiments, the second protective cover and the second grounding layer can be glued, laminated, or thermally bonded together.

In various examples, the first protective cover, the first grounding layer, the first compressible insulating layer, the sensor layer, the second compressible insulating layer, the second grounding layer, the second protective cover form an insole for a shoe.

Subsequently, method 700 of FIG. 7 includes an activity 784 of providing a processing module and/or an electrical device. This processing module performs a measurement of the capacitance, which can be used to calculate distance between the sensors and ground planes. This distance changes with the applied forces comprised of the compression of the insulating layers. In some examples, method 700 can include providing a processing module similar or identical to processing module 113 of FIG. 1. In other examples, activity 784 can include providing an electrical device that is similar or identical to electrical device 110 of FIG. 1. The processing module and/or electrical device of activity 784 are not part of the insole. After activity 784, method 700 is complete.

Although the invention has been described with reference to specific embodiments, it will be understood by those skilled in the art that various changes may be made without departing from the spirit or scope of the invention. Accordingly, the disclosure of embodiments of the invention is intended to be illustrative of the scope of the invention and is not intended to be limiting. It is intended that the scope of the invention shall be limited only to the extent required by the appended claims. For example, to one of ordinary skill in the art, it will be readily apparent that activities 770-784 may be comprised of many different activities, procedures and be performed by many different modules, in many different orders that any element of FIG. 1 or 2 may be modified and that the foregoing discussion of certain of these embodiments does not necessarily represent a complete description of all possible embodiments.

All elements claimed in any particular claim are essential to the embodiment claimed in that particular claim. Consequently, replacement of one or more claimed elements constitutes reconstruction and not repair. Additionally, benefits, other advantages, and solutions to problems have been described with regard to specific embodiments. The benefits, advantages, solutions to problems, and any element or elements that may cause any benefit, advantage, or solution to occur or become more pronounced, however, are not to be construed as critical, required, or essential features or elements of any or all of the claims, unless such benefits, advantages, solutions, or elements are stated in such claim.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

What is claimed is:

1. An insole for a shoe to be worn on a foot of a user, the insole comprising:
an upper conductive ground plane layer;
an upper compressible insulating layer physically coupled to the upper conductive ground plane layer;
a conductive sensor layer physically coupled to the upper compressible insulating layer, the conductive sensor layer comprising one or more sensors are configured to measure a force applied to the insole by the foot of the user;
a lower compressible insulating layer physically coupled to conductive sensor layer;
a lower conductive ground plane layer physically coupled to the lower compressible insulating layer and electrically coupled to the upper conductive ground plane layer; and
at least one computational unit communicatively coupled to the one or more sensors, wherein:
the upper conductive ground plane layer and the lower conductive ground plane layer are configured to substantially electrically shield the upper compressible insulating layer, the conductive sensor layer, and the lower compressible insulating layer from the shoe and the foot of the user;
the one or more sensors are configured to measure at least one of a first change in a first distance between the upper conductive ground plane layer and the one or more sensors and a second change in a second distance between the lower conductive ground plane layer and the one or more sensors; and
the at least one computational unit is configured to determine a force applied to the insole using the at least one of the first change in the first distance or the second change in the second distance.

2. The insole of claim 1, further comprising:
a comfort layer physically coupled to the upper conductive ground plane layer and configured to be a first outer layer of the insole and further configured to physically touch the foot of the user when the user is wearing the shoe with the insole; and
a protective cover layer physically coupled the lower conductive ground plane layer and configured to be a second outer layer of the insole and further configured to physically touch a top surface of a bottom layer of the shoe when the insole is in the shoe.

3. The insole of claim 1, wherein:
the upper conductive ground plane layer and the lower conductive ground plane layer are configured to substantially electrically block parasitic capacitance.

4. The insole of claim 1, wherein:
the upper conductive ground plane layer has a top surface and a bottom surface opposite the top surface;
the upper compressible insulating layer has a top surface and a bottom surface opposite the top surface;
the conductive sensor layer has a top surface and a bottom surface opposite the top surface;
the lower compressible insulating layer has a top surface and a bottom surface opposite the top surface;
the lower conductive ground plane layer has a top surface and a bottom surface opposite the top surface;

the bottom surface of the upper conductive ground plane layer is physically coupled to the top surface of the upper compressible insulating layer;

the bottom surface of the upper compressible insulating layer is physically coupled to the top surface of the conductive sensor layer;

the bottom surface of the conductive sensor layer is physically coupled to the top surface of the lower compressible insulating layer; and the bottom surface of the lower compressible insulating layer is physically coupled to the top surface of the lower conductive ground plane layer.

5. The insole of claim 1, wherein:
the upper conductive ground plane layer, the lower conductive ground plane layer, and the conductive sensor layer are configured to form a three-layer capacitor.

6. The insole of claim 1, wherein:
the one or more sensors comprise:
a heel sensor located in a region of the conductive sensor layer under where a heel of the foot of the user is located when the user is wearing the shoe with the insole; and
a ball sensor located in a region of the conductive sensor layer under where a ball of the foot of the user is located when the user is wearing the shoe with the insole.

7. The insole of claim 1, wherein:
the conductive sensor layer comprises the at least one computational unit.

8. The insole of claim 1, wherein:
the conductive sensor layer comprises a communication device configured to wirelessly communicate information regarding the force and other information regarding the user to one or more remote communication devices.

9. The insole of claim 8, wherein:
the upper conductive ground plane layer and the lower conductive ground plane layer comprise at least one conductive fabric; and
the upper compressible insulating layer and the lower compressible insulating layer comprise at least one of sheet rubber compounds, compressible plastic materials, or cell foams.

10. The insole of claim 1, wherein:
the one or more sensors are configured to measure the first change in the first distance and measure the second change in the second distance by electrically determining the first change in the first distance and the second change in the second distance.

11. A system for measuring information from the foot of a user, the system comprising:
an insole comprising:
a first protective cover configured to be a first outer layer of the insole;
a first grounding layer, a top surface of the first grounding layer is physically coupled to a bottom surface of the first protective cover;
a first compressible insulating layer, a top surface of the first compressible insulating layer is physically coupled to a bottom surface of the first grounding layer;
a sensor layer comprising a heel sensor and a ball sensor, a top surface of the sensor layer is physically coupled to a bottom surface of the first compressible insulating layer;
a second compressible insulating layer, a top surface of the second compressible insulating layer is physically coupled to a bottom surface of the sensor layer;
a second grounding layer, a top surface of the second grounding layer is physically coupled to a bottom surface of second compressible insulating layer, the second grounding layer is electrically coupled to the first grounding layer such that the first grounding layer and the second grounding layer substantially electrically isolate the insole from the shoe and the foot of the user; and
a second protective cover, a top surface of the second protective cover is physically coupled a bottom surface of the second grounding layer and further configured to be a second outer layer of the insole; and
at least one computational unit communicatively coupled to the heel sensor and the ball sensor,
wherein:
the first grounding layer, the second grounding layer and the sensor layer are electrically coupled to form a three-layer capacitor and the ball sensor and the heel sensor are configured to measure changes in capacitance between at least two of the first grounding layer, the second grounding layer and the sensor layer when a force is applied to the insole; and
the at least one computational unit is configured to determine a magnitude of the force applied to the insole using at least the changes in the capacitance between the at least two of the first grounding layer, the second grounding layer and the sensor layer.

12. The system of claim 11, wherein:
the sensor layer further comprises the at least one computational unit.

13. The system of claim 11, wherein:
the heel sensor located in a region of the sensor layer under where a heel of the foot of the user is located above when the user is wearing the shoe with the insole; and
a ball sensor located in a region of the sensor layer under where a ball of the foot of the user is located above when the user is wearing the shoe with the insole.

14. The system of claim 11, further comprising:
an electrical device comprising a wireless receiver,
wherein:
the sensor layer further comprises a wireless transmitter configured to transmit the magnitude of the force and other information related to the insole to the wireless receiver of the electrical device.

15. The system of claim 11, wherein:
a length of the first grounding layer is substantially equal to a length of the insole;
a width of the first grounding layer is substantially equal to a width of the insole;
a length of the second grounding layer is substantially equal to the length of the insole; and
a width of the second grounding layer is substantially equal to the width of the insole.

16. The system of claim 11, wherein:
the first protective cover comprises compressible foam; and
the second protective cover comprises an abrasion resistant coat.

17. The system of claim 11, wherein:
the second grounding layer is electrically coupled to the first grounding layer such that the first grounding layer and the second grounding layer substantially electrically isolate the heel sensor and the ball sensor from any electrical charge on the foot of the user.

18. A method of providing an insole for a shoe, the insole configured to be placed in the shoe and the shoe is configured to be placed on a foot of a user, the method comprising:

providing an upper conductive ground plane layer;
providing an upper compressible insulating layer;
physically coupling the upper compressible insulating layer to the upper conductive ground plane layer;
providing a conductive sensor layer, the conductive sensor layer comprises one or more sensors are configured to measure a force applied to the insole;
physically coupling the upper compressible insulating layer to conductive sensor layer;
providing a lower compressible insulating layer;
physically coupling the lower compressible insulating layer to conductive sensor layer;
providing a lower conductive ground plane layer;
physically coupling the lower conductive ground plane layer to the upper conductive ground plane layer;
electrically coupling the lower conductive ground plane layer to the upper conductive ground plane layer such that the upper conductive ground plane layer and the lower conductive ground plane layer are configured to substantially electrically shield the upper compressible insulating layer, the conductive sensor layer, and the lower compressible insulating layer from the shoe and the foot of the user; and
providing at least one computational unit communicatively coupled to the one or more sensors,
wherein:
the one or more sensors are configured to measure at least one of a first change in a first distance between the upper conductive ground plane layer and the one or more sensors or a second change in a second distance between the lower conductive ground plane layer and the one or more sensors; and
the at least one computational unit is configured to determine a force applied to the insole using at least one of the first change in the first distance or the second change in the second distance.

19. The method of claim 18, further comprising:
providing a comfort layer configured to be a first outer layer of the insole and further configured to physically touch the foot of the user when the user is wearing the shoe with the insole;
physically coupling the comfort layer to the upper conductive ground plane layer;
providing a protective cover layer configured to be a second outer layer of the insole and further configured to physically touch a top of a bottom layer of the shoe; and
physically coupling the protective cover layer to the lower conductive ground plane layer.

20. The method of claim 18, wherein:
the upper conductive ground plane layer and the lower conductive ground plane layer are electrically coupled such that the upper conductive ground plane layer and the lower conductive ground plane layer substantially electrically block any parasitic capacitance emanating from the foot of the user.

* * * * *